US007071362B2

(12) United States Patent
Sugawara et al.

(10) Patent No.: US 7,071,362 B2
(45) Date of Patent: Jul. 4, 2006

(54) PROCESS FOR PRODUCING ALICYCLIC ALDEHYDES

(75) Inventors: Tomohiro Sugawara, Okayama (JP); Fumiya Zaima, Okayama (JP); Atsushi Okoshi, Okayama (JP); Kinji Kato, Okayama (JP); Masato Inari, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/924,811

(22) Filed: Aug. 25, 2004

(65) Prior Publication Data

US 2005/0054879 A1 Mar. 10, 2005

(30) Foreign Application Priority Data

Aug. 27, 2003 (JP) ............................ 2003-302814
Sep. 5, 2003 (JP) ............................ 2003-313903

(51) Int. Cl.
*C07C 47/28* (2006.01)
*C07C 47/32* (2006.01)

(52) U.S. Cl. ...................................... 568/420; 568/443

(58) Field of Classification Search ................ 568/420, 568/443

See application file for complete search history.

(56) References Cited

U.S. PATENT DOCUMENTS 4,258,205 A * 3/1981 Van Berkel et al. ........ 560/231

FOREIGN PATENT DOCUMENTS

DE 37 18 870 12/1988
JP 10-195020 7/1998

OTHER PUBLICATIONS

Communication and European Search Report dated Nov. 8, 2004, for No. EP 04 10 4047.

Sulzbacher, et al. "The Preparation of Some Cyclic Acetals", J. Am. Chem. Soc., vol. 70, No. 8, 1948, pp. 2827-2828.

Martin, et al., "Halogenated Carbonyl Ylides in the Reactions of Mercurial Dihalocarbene Precursors with Substituted Benzaldehydes", J. Org. Chem. vol. 43, No. 6, 1978, pp. 1071-1076.

Nielsen, et al., "Synthesis of 3,5,12-Triazawurtzitanes (3,5,12-Triazatetracyclo[$5.3.1.1^{2,0}.0^{4,9}$]dodecanes)", J. Org. Chem., 1987, vol. 52, No. 9, pp. 1656-1662.

Marconi, et al., "Nanostructured ruthenium on y-$Al_2O_3$ catalysts for the efficient hydrogenation of aromatic compounds", Journal of Organometallic Chemistry 689 (2004), pp. 639-646.

* cited by examiner

*Primary Examiner*—Sikarl A. Witherspoon
(74) *Attorney, Agent, or Firm*—Antonelli, Terry, Stout and Kraus, LLP.

(57) ABSTRACT

In the production of an alicyclic aldehyde, a starting aromatic aldehyde is converted into an aromatic acetal for protecting the formyl group. The aromatic ring of the aromatic acetal is then hydrogenated to convert the aromatic acetal into an alicyclic acetal, which is then hydrolyzed to cleave the acetal protecting group to obtain the aimed alicyclic aldehyde.

25 Claims, No Drawings

PROCESS FOR PRODUCING ALICYCLIC ALDEHYDES

BACKGROUND OF THE INVENTION

1. Field of the Invention

The present invention relates to a process for producing a high-purity alicyclic aldehyde that is used as a raw material for perfumes or intermediate products of medicines and agricultural chemicals in a high yield and in an industrially advantageous manner, and more particularly to a process for producing an alicyclic aldehyde having a structure derived from the hydrogenation of the aromatic ring of a corresponding aromatic aldehyde.

2. Description of the Prior Art

Known methods for the production of alicyclic aldehydes include a method of reducing an ester of a corresponding alicyclic carboxylic acid (U.S. Pat. No. 3,660,416); a method of oxidizing a corresponding alicyclic alcohol (U.S. Pat. No. 3,901,896); a method of reducing a corresponding alicyclic carboxylic acid (EP 439115A and WO 00/12457); and a method of formylating a corresponding alicyclic olefin with hydrogen and carbon monoxide or carbon dioxide (JP 5-246925A and JP 2001-233795A). However, the method of reducing the ester of alicyclic carboxylic acid requires a step of converting an alicyclic carboxylic acid into its ester to complicate the process. Also, in the method of reducing the alicyclic carboxylic acid, the reduction reaction must be carried out under severe conditions, or compounds that are not readily industrially available must be used. Further, in the method using the corresponding olefin or alcohol as the starting material, an additional reaction step such as Diels-Alder reaction is required.

SUMMARY OF THE INVENTION

An object of the present invention is to provide a process for producing an alicyclic aldehyde in a high yield and in an industrially advantageous manner.

As a result of extensive research in view of achieving the above object, the inventors have found that the aimed alicyclic aldehyde is produced by acetalizing an aromatic aldehyde to protect the formyl group, hydrogenating the resultant aromatic acetal to obtain an alicyclic acetal, and then hydrolyzing the obtained alicyclic acetal to cleave the protecting group. The inventors have further found that the alicyclic aldehyde is produced more selectively by hydrogenating the aromatic acetal in the presence of an acid or an alkali.

The present invention has been accomplished on the basis of this finding.

Thus, the present invention provides a process for producing an alicyclic aldehyde, comprising the following steps of:

(A) acetalizing an aromatic aldehyde with an alcohol into an aromatic acetal;

(B) hydrogenating the aromatic acetal produced in the step A into an alicyclic acetal; and (C) hydrolyzing the alicyclic acetal produced in the step B into the alicyclic aldehyde.

The step B is preferably conducted in the presence of a noble metal-containing catalyst and preferably further in the presence of an acid or an alkali.

DETAILED DESCRIPTION OF THE INVENTION

Step A: Acetalization of Aromatic Aldehyde

The aromatic acetal is produced, for example, by acetalizing the aromatic aldehyde with an acetalizing agent such as alcohols. The method of producing the aromatic acetal from the aromatic aldehyde is described below.

The starting aromatic aldehyde is not particularly limited as far as it has at least one formyl group on its aromatic ring, and may be appropriately selected from various compounds according to the end use of the final products.

Examples of the aromatic aldehyde include benzaldehyde, p-tolualdehyde, o-tolualdehyde, m-tolualdehyde, 2,4-dimethyl benzaldehyde, 2,5-dimethylbenzaldehyde, 3,4-dimethylbenzaldehyde, 2,4,5-trimethylbenzaldehyde, 2,4,6-trimethylbenzaldehyde, p-n-propylbenzaldehyde, o-n-propylbenzaldehyde, m-n-propylbenzaldehyde, p-isopropylbenzaldehyde, o-isopropylbenzaldehyde, m-isopropylbenzaldehyde, p-n-butylbenzaldehyde, o-n-butylbenzaldehyde, m-n-butylbenzaldehyde, p-isobutylbenzaldehyde, o-isobutylbenzaldehyde, m-isobutylbenzaldehyde, p-sec-butylbenzaldehyde, o-sec-butylbenzaldehyde, m-sec-butylbenzaldehyde, p-tert-butylbenzaldehyde, o-tert-butylbenzaldehyde, m-tert-butylbenzaldehyde, α-naphthaldehyde, β-naphthaldehyde, 2-tetralin carbaldehyde, 4-biphenyl carbaldehyde, p-hydroxybenzaldehyde, o-hydroxybenzaldehyde, p-methoxybenzaldehyde, o-methoxybenzaldehyde, phthalaldehyde, isophthalaldehyde and terephthalaldehyde.

Of these aromatic aldehydes, in view of industrial utilization of the alicyclic aldehyde to be produced, preferred are benzaldehyde, p-tolualdehyde, 2,4-dimethylbenzaldehyde, 3,4-dimethylbenzaldehyde, 2,4,5-trimethylbenzaldehyde, p-isopropylbenzaldehyde and p-isobutylbenzaldehyde. The aromatic aldehydes of commercially available grades may be sufficiently used.

Examples of the acetalizing agent include alcohols such as methanol, ethanol, 1-propanol, 2-propanol, 1-butanol, 2-methyl-1-propanol, 2-butanol, 2-methyl-2-propanol, ethylene glycol, 1,2-propane diol, 1,3-propane diol, neopentyl glycol, pentaerythritol and sorbitol, with ethylene glycol, pentaerythritol and sorbitol being particularly preferred. The amount of the acetalizing agent to be used is preferably 5 to 100 mol for the monohydric compound and preferably 2 to 100 mol for the polyhydric compound, each per one mole of the aromatic aldehyde.

The above aromatic aldehyde and the acetalizing agent may be appropriately combined for the acetlization. For example, the combination of benzaldehyde with ethylene glycol provides 2-phenyl-1,3-dioxolane. Similarly, the combination of 2,4-dimethylbenzaldehyde with ethylene glycol provides 2-(2,4-dimethylphenyl)-1,3-dioxolane.

In a preferred embodiment of the invention, the aromatic aldehyde is acetalized with an acetalizing agent in a solvent in the presence of an acid catalyst under reflux. Since the acetalization reaction is a dehydration reaction, it is required to remove the water being generated during the reaction from the reaction system. The reaction temperature is selected from the refluxing temperature range of the solvent used. The acetalization is generally completed within 5 to 48 h.

The acetalization is carried out preferably in the presence of a solvent. The preferred solvents are aromatic or aliphatic hydrocarbons having 6 to 9 carbon atoms. Examples of the solvent include hexane, heptane, octane, nonane, benzene and toluene. The solvent is used in an amount so as to make the concentration of the aromatic aldehyde in the reaction solution into preferably 1 to 50% by weight, more preferably 5 to 40% by weight.

The acid catalyst is selected from p-toluenesulfonic acid, hydrochloric acid, sulfuric acid, acetic acid, nitric acid and zeolite, and used in an amount of preferably 0.01 to 1.0 mol or 0.5 to 10 g (for zeolite) per one mole of the aromatic aldehyde.

After the acetalization, the reaction product solution is preferably distilled to obtain the aromatic acetal, which is then subjected to hydrogenation in the step B. The distillation residue may be recycled to an acetalization vessel. The proportion of the distillation residue to be recycled may be appropriately determined according to the reaction conditions. Next, the hydrogenation of the thus obtained aromatic acetal is described.

Step B: Hydrogenation of Aromatic Acetal

The aromatic acetal is hydrogenated by hydrogen gas in the presence of a hydrogenation catalyst, in the presence or absence of a solvent, and preferably in the presence of an acid or an alkali.

Examples of the solvent include hydrocarbons, halogenated hydrocarbons, esters, ketones, ethers, alcohols, aliphatic acids and water, with methanol and tetrahydrofuran being preferred. When the solvent is used, the concentration of the aromatic acetal in the reaction solution is preferably 5 to 50% by weight and more preferably 10 to 40% by weight.

By adding the acid or the alkali into the reaction solution, the hydrogenation is promoted to increase the selectivity to the alicyclic acetal.

Examples of the acids include saturated aliphatic acids such as acetic acid, propionic acid and butyric acid; and inorganic acids such as hydrochloric acid, sulfuric acid, nitric acid, zeolite and heteropoly-acids. The acid is used so that the acid concentration in the reaction solution is preferably 0.1 to 20% by weight and more preferably 0.5 to 10% by weight.

Examples of the alkali include amines such as n-propylamine, isopropylamine, diethylamine and triethylamine; and alkali salts of inorganic acids such as sodium carbonate, potassium carbonate, sodium acetate, potassium acetate, sodium phosphate, sodium hydroxide, potassium hydroxide and lithium hydroxide, with triethylamine and sodium carbonate being preferred. The alkali is used so that the alkali concentration in the reaction solution is preferably 0.1 to 20% by weight and more preferably 0.5 to 10% by weight.

A noble metal-containing catalyst is preferably used as the hydrogenation catalyst. The noble metal is preferably at least one metal selected from the group consisting of rhodium, palladium and ruthenium, with the sole use of rhodium being more preferred. The noble metal is preferably supported on a carrier such as carbon and alumina, particularly, on alumina. The shape of the catalyst is not particularly limited, and may be selected from a powder, and crushed particles and pellets for fixed bed according to the hydrogenation manner. The amount of the noble metal supported on the carrier is preferably 0.5 to 30% by weight and more preferably 0.5 to 10% by weight on the basis of the total weight of the catalyst.

In the production process of the present invention, the hydrogenation may be carried out in either batch-wise manner or continuous manner.

In the batch-wise hydrogenation, 100 parts by weight of the aromatic acetal is hydrogenated under a hydrogen partial pressure of 0.01 MPa or higher (pressure at the reaction temperature, the same is applied below) in the presence of the noble metal-containing catalyst in an amount of 0.5 to 10 parts by weight in terms of the noble metal. If the amount of the noble metal used is less than 0.5 part by weight per 100 parts by weight of the aromatic acetal, the hydrogenation may fail to proceed sufficiently. An amount exceeding 10 parts by weight creates no additional catalytic effect and is rather economically disadvantageous. The noble metal-containing catalyst is used preferably 0.5 to 5.0 parts by weight per 100 parts by weight of the aromatic acetal in terms of noble metal.

If the hydrogen partial pressure is less than 0.01 MPa, it becomes difficult to achieve a desired conversion, thereby failing to achieve the object of the present invention. The hydrogen partial pressure is preferably 0.01 to 15 MPa. The hydrogenation temperature is preferably 0 to 180° C. The hydrogenation time may vary depending upon the reaction temperature and other conditions, and therefore, is not critical. Usually, the reaction time of 30 to 360 min is sufficient for completing the hydrogenation.

In the continuous flow hydrogenation, the aromatic acetal is hydrogenated under a hydrogen partial pressure of 0.01 MPa or higher while feeding the aromatic acetal into a packed bed of the noble metal-containing catalyst at a rate of 1 to 100 parts by weight/h per one part by weight of the noble metal, i.e., at a weight hourly space velocity (WHSV) of 1 to 100 $h^{-1}$. WHSV of less than 1 $h^{-1}$ is unpractical because of low production efficiency. WHSC exceeding 100 $h^{-1}$ fails to achieve a desired conversion, resulting in failure to accomplish the object of the present invention. WHSV is preferably 3 to 50 $h^{-1}$.

The hydrogen partial pressure and hydrogenation temperature are the same as described above with respect to the batch-wise manner. The continuous hydrogenation may be carried out in either a liquid filling system or a liquid-through system, with the liquid-through system being preferred.

The reactor used in the hydrogenation may be made of stainless steel such as SUS304, SUS316 and SUS316L. Ordinary pressure reactors made of iron or stainless steel which have been subjected to glass lining may be also usable.

When methanol or tetrahydrofuran is used as the solvent, the produced alicyclic acetal is dissolved in the solvent. After removing the noble metal-containing catalyst by filtration, the filtrate is distilled to obtain the alicyclic acetal separately from the solvent.

The starting aromatic acetal may be hydrogenated either completely or partially depending upon the kind of the aimed alicyclic acetal. Products of complete hydrogenation may include 2-cyclohexyl-1,3-dioxilane from 2-phenyl-1,3-dioxolane, and 2-(2,4-dimethylcyclohexyl)-1,3-dioxolane from 2-(2,4-dimethylphenyl)-1,3-dioxolane. Products of partial hydrogenation may include a compound having a tetralin skeleton produced from a starting aromatic acetal having a naphthalene skeleton, and a compound having both a benzene ring and a cyclohexane ring which is produced from a starting aromatic acetal having two benzene rings by hydrogenating only one of the benzene rings into a cyclohexane ring.

After completion of the hydrogenation, the reaction product solution may be distilled to separate the alicyclic acetal. The distillation residue may be recycled to the reactor for hydrogenation. The proportion of the amount of distillation residue to be recycled may be determined according to the hydrogenation conditions.

Step C: Hydrolysis of Alicyclic Acetal

The alicyclic acetal obtained in the step B is then hydrolyzed into the alicyclic aldehyde. For example, 2-cyclohexyl-1,3-dioxolane is hydrolyzed into cyclohexylaldehyde, and 2-(2,4-dimethylcyclohexyl)-1,3-dioxolane into 2,4-dimethylcyclohexyaldehyde.

The hydrolysis of the alicyclic acetal is preferably carried out in water as a solvent, more preferably in the presence of an acid such as acetic acid, hydrochloric acid and sulfuric acid, and still more preferably in the presence of acetic acid. The amount of water to be used is preferably 0.1 to 100 times by weight the alicyclic acetal. The amount of the acid to be used is preferably 0.1 to 10 mol per one mole of the alicyclic acetal. Water and the acid of ordinary grade may be used without any pre-treatment. If the amounts of water and the acid are less than the above ranges, the rate of hydrolysis is low. If exceeding the above ranges, the recovery of the resultant alicyclic aldehyde unfavorably becomes difficult.

To effectively conduct the hydrolysis, the temperature is preferably 0 to 100° C. The hydrolysis proceeds by merely stirring the mixed solution of the alicyclic acetal, water and the acid, or by refluxing the mixed solution under heating. The hydrolysis may be completed by maintaining the reaction system at the hydrolysis temperature for about 1 to 360 min under stirring.

The hydrolysis is preferably conducted in an inert gas atmosphere such. as nitrogen gas atmosphere.

In addition, a secondary solvent such as hydrocarbons, halogenated hydrocarbons, esters, ketones, ethers and aliphatic acids, each having a boiling point of 50° C. or higher, may be added to the hydrolysis system.

After completion of the hydrolysis, the reaction product solution may be subjected, if desired, to neutralization with alkali or extraction with an organic solvent such as acetic acid esters. The reaction solvent or the extraction solvent is removed by distillation. The residue is distilled by heating to the boiling point of the alicyclic aldehyde to obtain the alicyclic aldehyde as the final product.

The solvents removed by distillation and the residue after distilling the alicyclic aldehyde may be recycled to the reactor for hydrolysis. The proportions of the solvents and the residue to be recycled to the hydrolysis reactor may be determined by taking the accumulation of impurities within the hydrolysis system into account.

As described above, according to the present invention, a high-purity alicyclic aldehyde is produced by a simple process and in an industrially advantageous manner.

The present invention will be described in more detail below with reference to the following examples. However, these examples are only illustrative and not intended to limit the invention thereto.

EXAMPLE 1

A 500-mL three-necked flask equipped with a reflux condenser having a Dean-Stark water trap was charged with 5.0 g of benzaldehyde, 29.3 g of ethylene glycol, 0.09 g of p-toluenesulfonic acid monohydrate and 250 mL of benzene, and the contents were refluxed for 21 h. The resultant reaction solution was allowed to stand for cooling and then washed with 50 mL of a saturated aqueous solution of sodium hydrogen carbonate and 50 mL of water. After vacuum-concentrating the organic phase, 6.3 g of the aimed 2-phenyl-1,3-dioxolane was obtained by vacuum distillation (89% yield).

After charging 4 g of 2-phenyl-1,3-dioxolane, 0.4 g of a Rh-alumina powdery catalyst (5% by weight of 2-phenyl-1,3-dioxolane in terms of Rh), 29.5 mL of methanol and 0.5 mL of acetic acid into a 100-mL shaking autoclave, the inner atmosphere was replaced with nitrogen gas twice and then with hydrogen gas three times. After adjusting the hydrogen pressure to 4.0 MPa, the temperature was raised to proceed the hydrogenation at 40° C. for 120 min. The reaction product solution taken out of the autoclave was filtered by a vacuum filter having a 1.0 μm membrane filter made of polytetrafluoroethylene (PTFE) to remove the catalyst, thereby obtaining a colorless transparent filtrate.

The filtrate was distilled by a rotary evaporator to remove the organic solvent, and the residue was analyzed by gas chromatography. The conversion of 2-phenyl-1,3-dioxolane was 96% and the selectivity to 2-cyclohexyl-1,3-dioxolane was 87%. By purifying the residue by distillation, 2-cyclohexyl-1,3-dioxolane having a purity of 98.5% was obtained.

Into a 200-mL round bottom flask, were charged 3.0 g of the purified 2-cyclohexyl-1,3-dioxolane, 40 mL of acetic acid and 10 mL of water, and the mixture was stirred at room temperature for 40 min. After adding 100 mL of a saturated aqueous solution of sodium hydrogen carbonate, the reaction product solution was extracted with 100 mL of ethyl acetate twice. By vacuum-concentrating the organic phase, 2.1 g of cyclohexylaldehyde having a purity of 99% or higher free from 2-cyclohexyl-1,3-dioxolane was obtained (94% yield). The yield of cyclohexylaldehyde based on the starting aromatic aldehyde was 70%.

EXAMPLE 2

The procedure of Example 1 was repeated except that the hydrogenation of the aromatic acetal was conducted under the following conditions: Into a 100-mL shaking autoclave, were charged 4.0 g of 2-phenyl-1,3-dioxolane, 0.8 g of a Rh-carbon powdery catalyst having a water content of 50% (5% by weight of 2-phenyl-1,3-dioxolane in terms of Rh) and 30 mL of tetrahydrofuran, and the inner atmosphere was replaced with nitrogen gas twice and then with hydrogen gas three times. After adjusting the hydrogen pressure to 4.0 MPa, the temperature was raised to proceed the hydrogenation at 70° C. for 120 min. The reaction product solution taken out of the autoclave was filtered by a vacuum filter having a 1.0 μm PTFE membrane filter to remove the catalyst, thereby obtaining a colorless transparent filtrate.

The filtrate was distilled by a rotary evaporator to remove the organic solvent, and the residue was analyzed by gas chromatography. The conversion of 2-phenyl-1,3-dioxolane was 100% and the selectivity to 2-cyclohexyl-1,3-dioxolane was 11%. The yield of cyclohexylaldehyde based on the starting aromatic aldehyde was 16% and the purity was 99% or higher.

EXAMPLE 3

The procedure of Example 1 was repeated except for using 2,4-dimethylbenzaldehyde as the starting aromatic aldehyde. In the hydrogenation, the conversion of 2-(2,4-dimethylphenyl)-1,3-dioxolane was 95% and the selectivity to 2-(2,4-dimethylcyclohexyl)-1,3-dioxolane was 85%. The yield of 2,4-dimethylcyclohexylaldehyde based on the starting aromatic aldehyde was 68% and the purity was 99% or higher.

COMPARATIVE EXAMPLE 1

Direct Hydrogenation of Aromatic Aldehyde Using Rh-carbon Catalyst

Into a 100-mL shaking autoclave, were charged 4.0 g of 2,4-dimethylbenzaldehyde, 0.8 g of a Rh-carbon powdery catalyst having a water content of 50% (5% by weight of 2,4-dimethylbenzaldehyde in terms of Rh) and 32 g of tetrahydrofuran, and the inner atmosphere was replaced with nitrogen gas twice and then with hydrogen gas three times. After adjusting the hydrogen pressure to 4.0 MPa, the temperature was raised to proceed the hydrogenation at 70° C. for 120 min. The reaction product solution taken out of the autoclave was filtered by a vacuum filter having a 1.0 μm PTFE membrane filter to remove the catalyst, thereby obtaining a colorless transparent filtrate.

The filtrate was distilled by a rotary evaporator to remove tetrahydrofuran, and the residue was analyzed by gas chromatography. The conversion of 2,4-dimethylbenzaldehyde was 99%, and pseudo-cumene was obtained in a selectivity of 95%. No 2,4-dimethylcyclohexylaldehyde as the aimed product was obtained.

COMPARATIVE EXAMPLE 2

Direct Hydrogenation of Aromatic Aldehyde Using Ru-carbon Catalyst

Into a 100-mL shaking autoclave, were charged 4.0 g of 2,4-dimethylbenzaldehyde, 0.8 g of a Ru-carbon powdery catalyst having a water content of 50% (5% by weight of 2,4-dimethylbenzaldehyde in terms of Ru) and 32 g of tetrahydrofuran, and the inner atmosphere was replaced with nitrogen gas twice and then with hydrogen gas three times. After adjusting the hydrogen pressure to 4.0 MPa, the temperature was raised to proceed the hydrogenation at 100° C. for 300 min. The reaction product solution taken out of the autoclave was filtered by a vacuum filter having a 1.0 μm PTFE membrane filter to remove the catalyst, thereby obtaining a colorless transparent filtrate.

The filtrate was distilled by a rotary evaporator to remove tetrahydrofuran, and the residue was analyzed by gas chromatography. The conversion of 2,4-dimethylbenzaldehyde was 99%, and 2,4-dimethylbenzyl alcohol was obtained in a selectivity of 95%. No 2,4-dimethylcyclohexylaldehyde as the aimed product was obtained.

EXAMPLE 4

A 500-mL three-necked flask equipped with a reflux condenser having a Dean-Stark water trap was charged with 5.0 g of benzaldehyde, 29.3 g of ethylene glycol, 0.09 g of p-toluenesulfonic acid monohydrate and 250 mL of benzene, and the contents were refluxed for 21 h. The resultant reaction solution was allowed to stand for cooling and then washed with 50 mL of a saturated aqueous solution of sodium hydrogen carbonate and 50 mL of water. After vacuum-concentrating the organic phase, 6.3 g of the aimed 2-phenyl-1,3-dioxolane was obtained by vacuum distillation (89% yield).

After charging 4.0 g of 2-phenyl-1,3-dioxolane, 0.8 g of a Rh-carbon powdery catalyst having a water content of 50% (5% by weight of 2-phenyl-1,3-dioxolane in terms of Rh), 30 mL of tetrahydrofuran and 1.6 g of triethylamine into a 100-mL shaking autoclave, the inner atmosphere was replaced with nitrogen gas twice and then with hydrogen gas three times. After adjusting the hydrogen pressure to 4.0 MPa, the temperature was raised to proceed the hydrogenation at 70° C. for 120 min. The reaction product solution taken out of the autoclave was filtered by a vacuum filter having a 1.0 μm membrane filter made of polytetrafluoroethylene (PTFE) to remove the catalyst, thereby obtaining a colorless transparent filtrate.

The filtrate was distilled by a rotary evaporator to remove the organic solvent, and the residue was analyzed by gas chromatography. The conversion of 2-phenyl-1,3-dioxolane was 38% and the selectivity to 2-cyclohexyl-1,3-dioxolane was 51%. By purifying the residue by distillation, 2-cyclohexyl-1,3-dioxolane having a purity of 98.5% was obtained.

Into a 200-mL round bottom flask, were charged 3.0 g of the purified 2-cyclohexyl-1,3-dioxolane, 40 mL of acetic acid and 10 mL of water, and the mixture was stirred at room temperature for 40 min. After adding 100 mL of a saturated aqueous solution of sodium hydrogen carbonate, the reaction product solution was extracted with 100 mL of ethyl acetate twice. By vacuum-concentrating the organic phase, 2.1 g of cyclohexyl aldehyde having a purity of 99% or higher free from 2-cyclohexyl-1,3-dioxolane was obtained (94% yield). The yield of cyclohexylaldehyde based on the starting aromatic aldehyde was 16%.

EXAMPLE 5

The procedure of Example 4 was repeated except that the hydrogenation of the aromatic acetal was conducted at 90° C. In the hydrogenation, the conversion of 2-phenyl-1,3-dioxolane was 95% and the selectivity to 2-cyclohexyl-1,3-dioxolane was 48%. The yield of cyclohexylaldehyde based on the starting aromatic aldehyde was 38%, and the purity was 99% or higher.

EXAMPLE 6

The procedure of Example 5 was repeated except for changing the initial charge for the hydrogenation to 4.0 g of 2-phenyl-1,3-dioxolane, 0.8 g of a Rh-carbon powdery catalyst having a water content of 50% (5% by weight of 2-phenyl-1,3-dioxolane in terms of Rh), 38 mL of tetrahydrofuran and 2.0 g of sodium carbonate. The conversion of 2-phenyl-1,3-dioxolane was 55% and the selectivity to 2-cyclohexyl-1,3-dioxolane was 41%. The yield of cyclohexylaldehyde based on the starting aromatic aldehyde was 19% and the purity was 99% or higher.

EXAMPLE 7

The procedure of Example 5 was repeated except for using 2,4-dimethylbenzaldehyde as the starting aromatic aldehyde. In the hydrogenation, the conversion of 2-(2,4-dimethylphenyl)-1,3-dioxolane was 95% and the selectivity to 2-(2,4-dimethylcyclohexyl)-1,3-dioxolane was 50%. The yield of 2,4-dimethylcyclohexylaldehyde based on the starting aromatic aldehyde was 40% and the purity was 99% or higher.

EXAMPLE 8

The procedure of Example 4 was repeated except for adding no triethylamine into the solvent for the hydrogenation of the aromatic acetal. In the hydrogenation, the conversion of 2-phenyl-1,3-dioxolane was 100% and the selectivity to 2-cyclohexyl-1,3-dioxolane was 13%. The yield of cyclohexylaldehyde based on the starting aromatic aldehyde was 11% and the purity was 99% or higher.

According to the present invention, a high-purity alicyclic aldehyde usable as perfumes, intermediates for medicines and agricultural chemicals, etc., is produced in a high yield and in an industrially advantageous manner.

What is claimed is:

1. A process for producing an alicyclic aldehyde, comprising the steps of:

(A) acetalizing an aromatic aldehyde with an alcohol into an aromatic acetal;

(B) hydrogenating the aromatic acetal produced in the step A into an alicyclic acetal; and (C) hydrolyzing the alicyclic acetal produced in the step B into the alicyclic aldehyde;

wherein the hydrogenation of the aromatic acetal in the step B is conducted in the presence of an acid.

2. The process according to claim 1, wherein the aromatic aldehyde is selected from the group consisting of benzaldehyde, p-tolualdehyde, 2,4-dimethylbenzaldehyde, 3,4-dimethylbenzaldehyde, 2,4,5-trimethylbenzaldehyde, p-isopropylbenzaldehyde, and p-isobutylbenzaldehyde.

3. The process according to claim 1, wherein said acetalizing is carried out in the presence of a solvent.

4. The process according to claim 3, wherein said solvent is selected from the group consisting of aromatic and aliphatic hydrocarbons having 6 to 9 carbon atoms.

5. The process according to claim 1, wherein said acetalizing is carried out in the presence of an acid catalyst.

6. The process according to claim 5, wherein said acid catalyst is selected from the group consisting of p-toluenesulfonic acid, hydrochloric acid, sulfuric acid, acetic acid, nitric acid and zeolite.

7. The process according to claim 1, wherein said acid is selected from the group consisting of acetic acid, propionic acid, butyric acid, hydrochloric acid, sulfuric acid, nitric acid, zeolite and heteropolyacids.

8. The process according to claim 1, wherein said acid is included in a reaction solution for said hydrogenating in an amount of 0.1 to 20% by weight.

9. The process according to claim 1, wherein the hydrogenation of the aromatic acetal in the step B is conducted in the presence of a noble metal-containing catalyst.

10. The process according to claim 9, wherein the noble metal-containing catalyst comprises the noble metal supported on carbon or alumina.

11. The process according to claim 9, wherein the noble metal is at least one metal selected from the group consisting of rhodium, palladium and ruthenium.

12. The process according to claim 1, wherein the acid is a saturated aliphatic acid and/or an inorganic acid.

13. The process according to claim 1, wherein the hydrogenation in the step B is conducted at 0 to 180° C. under a hydrogen partial pressure of 0.01 to 15 MPa.

14. A process for producing an alicyclic aldehyde, comprising the steps of:

(A) acetalizing an aromatic aldehyde with an alcohol into an aromatic acetal;

(B) hydrogenating the aromatic acetal produced in the step A into an alicyclic acetal; and (C) hydrolyzing the alicyclic acetal produced in the step B into the alicyclic aldehyde;

wherein the hydrogenation of the aromatic acetal in the step B is conducted in the presence of an alkali.

15. The process according to claim 14, wherein the hydrogenation of the aromatic acetal in the step B is conducted in the presence of a noble metal-containing catalyst.

16. The process according to claim 15, wherein the noble metal-containing catalyst comprises the noble metal supported on carbon or alumina.

17. The process according to claim 15, wherein the noble metal is at least one metal selected from the group consisting of rhodium, palladium and ruthenium.

18. The process according to claim 15, wherein the hydrogenation in the step B is conducted at 0 to 180° under a hydrogen partial pressure of 0.01 to 15 MPa.

19. The process according to claim 14, wherein said acetalizing is carried out in the presence of a solvent.

20. The process according to claim 14, wherein said acetalizing is carried out in the presence of an acid catalyst.

21. The process according to claim 14, wherein said alkali is included in a reaction solution for said hydrogenating in an amount of 0.1 to 20% by weight.

22. The process according to claim 15, wherein said alkali is selected from the group consisting of amines and alkali salts of inorganic acids.

23. The process according to claim 14, wherein said alkali is selected from the group consisting of n-propylamine, isopropylamine, diethylamine, triethylamine, sodium carbonate, potassium carbonate, sodium acetate, potassium acetate, sodium phosphate, sodium hydroxide, potassium hydroxide and lithium hydroxide.

24. The process according to claim 23, wherein said alkali is selected from the group consisting of triethylamine and sodium carbonate.

25. The process according to claim 14, wherein the alkali is amine and/or alkali salt of inorganic acid.

* * * * *